United States Patent
Woog et al.

Patent Number: 5,504,099
Date of Patent: Apr. 2, 1996

[54] INJECTION SOLUTIONS OF AZOSEMIDE WHICH ARE READY FOR INJECTION

[75] Inventors: Heinrich Woog, Laudenbach; Werner Gruber, Birkenau, both of Germany

[73] Assignee: Boehringer Mannheim GmbH, Mannheim, Germany

[21] Appl. No.: 387,819

[22] PCT Filed: Aug. 28, 1993

[86] PCT No.: PCT/EP93/02331

§ 371 Date: Feb. 24, 1995

§ 102(e) Date: Feb. 24, 1995

[87] PCT Pub. No.: WO94/05286

PCT Pub. Date: Mar. 17, 1994

[30] Foreign Application Priority Data

Aug. 31, 1992 [DE] Germany .................. 42 28 926.2

[51] Int. Cl.$^6$ .................................................... A61K 31/41
[52] U.S. Cl. .................................... 514/381; 514/869
[58] Field of Search .......................... 514/381, 869

[56] References Cited

U.S. PATENT DOCUMENTS 3,665,002  5/1972  Popelak et al. ............... 260/239.9

OTHER PUBLICATIONS

Martindale *The Extra Pharmacopoeia*, 30 ed (1992).

*Primary Examiner*—Richard L. Raymond
*Assistant Examiner*—Brian M. Burn
*Attorney, Agent, or Firm*—Nikaido, Marmelstein, Murray & Oram

[57] ABSTRACT

Aqueous injection solution that is ready-for-injection of a water-soluble, physiologically well-tolerated azosemide salt of an organic amide, which contains an organic solvent and if desired, a physiologically well-tolerated buffer and it concerns a process for the production of such an injection solution in which the salt is dissolved in a mixture which contains water, an organic solvent and, if desired, a physiologically well-tolerated buffer.

24 Claims, No Drawings

INJECTION SOLUTIONS OF AZOSEMIDE WHICH ARE READY FOR INJECTION

The present invention concerns aqueous injection solutions that are ready for injection and contain an organic solvent and at least one water-soluble, physiologically well-tolerated salt of azosemide as the active substance and it concerns a process for the production of such injection solutions.

Azosemide (2-chloro-5-(1H-tetrazol-5-yl)-$N^4$-2-thenyl-sulfanilamide) and water-soluble and physiologically well-tolerated salts thereof are used in medicine as a diuretic. Azosemide can also be used advantageously in combination with other diuretics or with beta blockers. Such combinations are described for example in the patent DE 25 56 001.

The problem that aqueous solutions which contain a canrenoate or combinations of such a salt with other diuretics are not stable due to the occurrence of inexplicable turbidities after the usual heat sterilization at 120° C. is solved in DE 25 56 001. As described in DE 25 56 001 the instability problem was previously circumvented by producing a lyophilisate of canrenoate or of a combination preparation containing it by dissolving the dry substance in an aqueous solvent. However, this preparation of an injection solution has disadvantages: the production of a lyophilisate is technically very time consuming. The lyophilisates have to be sterilized by a complicated sterilization by filtration, whereby it is not possible to avoid a proportion of unsterile lots containing pyrogens. Moreover, in addition to the really necessary solvent ampoule, a further handling is necessary to dissolve the lyophilisate.

According to DE 25 56 001 an improved stability is achieved by increasing the pH value of the solutions from a maximum of 10.2 to a value in the range between 10.2 and 11.2. Although the injection solutions stabilized in this manner have a usable venous tolerance, their high pH value is not physiologically acceptable.

The venous tolerance of an injection solution mainly depends on the following factors: pH value, buffer capacity and titration basicity or titration acidity.

The buffer capacity is generally defined as that equivalent amount (val of acid or lye) which is necessary to change the pH value of a solution with a volume of one liter by one pH unit. If monobasic acids or bases are used, the specification val/l of the acid or base used corresponds to the molar amount mol/l of this acid. Since in the present case the solutions used preferably have a pH value in the alkaline range, the buffer capacity can also be alternatively defined as that amount of for example a 0.1 normal HCl solution which is required to reduce the pH value of a solution of 1 l by one pH unit. The determination of the buffer capacity in therapeutic agents is based on the ready-to-use infusion solutions which, in addition to the active substance, contain auxiliary substances or additives which are usually used in pharmaceutical practice.

The titration basicity is generally defined as that amount of an acid which is necessary to adjust the pH value of a solution with a volume of one liter to the pH value of blood (about 7.2–7.4). In the present case the titration basicity can be alternatively defined as that amount of, for example, a 0.1 normal HCl solution which is necessary to reduce the pH of 1 l of a solution to that of blood. The titration basicity can be influenced by a change of the pH value and an appropriate selection of the buffer.

Injection solutions with a pH value in the range of the pH value of blood, i.e. between 7.2 and 7.4, or which have a higher pH value but a lower buffer capacity and a lower titration basicity, are very well tolerated by the veins. In the case of the solutions claimed in DE 25 56 001 the solubility among others of the active substance is increased by the increase in the pH value.

The solubility—for example—of the sodium salt of azosemide in water is actually good in particular at higher pH values (165 mg/100 ml at pH 8.0 and 201 mg/100 ml at pH 10.0). However, it was not possible to produce clear, stable injection solutions without recrystallisates in a pure aqueous medium even when their concentration of azosemide salt was below the saturation concentration. Moreover, it is desirable to have stable, clear azosemide injection solutions with a good venous tolerance that are ready for injection with a concentration of active substance which is much higher than the aforementioned saturation solubilities of the sodium salt i.e. in the range between about 2 to about 20 mg/1 ml solution.

Solutions with a concentration of azosemide active substance which, however, is at most at the lower end of the desired range, i.e. at about 2 mg/ml solution, can be produced by the aforementioned process in which a lyophilisate is produced as an intermediate product wherein the active substance is lyophilized in alkaline solution and the lyophilisate is then dissolved in water. The venous tolerance of the solutions prepared in this manner is also good even at pH values of about 10. However, the number of particles in the solutions produced in this manner is relatively high so that the criteria defined in the European Pharmacopoeia are often not fulfilled. Particles in the solutions prepared from lyophilisates are for example rubber particles which originate from the rubber stoppers used in the production of the lyophilisate or particles from incrustations which form during the lyophilisation and cannot be very readily completely dissolved.

The European Pharmacopoeia requires that injection solutions are almost free of suspended particles. Limits for visible and non-visible particles as well as methods for particle determination are laid down in the USP XXII (US-Pharmacopoeia= American Pharmacopoeia) and in the BP (British Pharmacopoeia) (the number of particles/container may be a maximum of 10,000 at particle diameters of $>=10$ µm and a maximum of 1000 at diameters of $>=25$ µm).

In addition there are the aforementioned inherent disadvantages of the lyophilisation process and the fact that at acceptable pH values it is not possible to achieve concentrations that are substantially above the lower limit for usable doses.

In addition it is known from DE-OS-24 23 550 and from the article "Renal Actions of Azosemide" by J. Greven and O. Heidenreich published in "Arzneimittel Forschung"/ Drugs Res. 31, (I), No. 2 (1981), pages 346– 350, that organic solvents can be added to aqueous solutions of alkali metal salts of azosemide. Experiments have shown (refer to Table 1 in the description) that the solubility of alkali metal salts of azosemide can be increased by the addition of such solvents. This is remarkable since these are salts whose lipophilic character is much less pronounced than that of the respective acids. However, the increase in solubility which can be achieved is not that remarkable that solutions can be produced which have a very good stability and at the same time have the desired high concentration of active substance.

The object is therefore to provide relatively highly concentrated azosemide preparations which are stable in solutions and which are physiologically well-tolerated when injected even at higher concentrations and a process for the production of such solutions. This object is achieved according to the features of patent claim 1 and with a process according to the features of claim 8.

The injection solution must be buffered during the sterilization for stabilization in order to prevent a pronounced reduction in the pH value. Azosemide salts are usually salts of a weak acid and a strong base and thus they have a buffer character themselves. Only when the buffering effect of the azosemide salts is too small, is it necessary to add additional buffer to the solution. When buffering it is essential to reach a compromise between an adequate stabilization and the lowest possible buffer capacity of the injection solution. A favourable factor in the case of the injection solutions according to the invention is that a strong buffering is not necessary to stabilize them so that it is possible to preserve the advantageously low buffer capacity of the solutions according to the invention. The solutions according to the invention survive a 20 minute sterilization at 121° C. without appreciable formation of particles or decomposition. Due to the low buffer capacity, the solutions according to the invention do not lead to significant changes in pH values at the site of injection so that an undiluted application is possible.

Experience up to now has shown that the solutions can completely unexpectedly be stored for at least three years at room temperature without the occurrence of turbidities or chemical changes in the active substance. These injection solutions also have a good venous tolerance despite the high concentration of active substance and despite the high content of organic solvents i.e. they can be administered intravenously in an undiluted form.

The meglumine-azosemide and triethanolamine-azosemide salt are particularly preferred as active substances for the injection solution according to the invention. Of these the azosemide salt of meglumine is most preferable since it has the lowest equivalent point and surprisingly the best solubility. The organic solvent is preferably selected from the group propylene glycol, polyethylene glycol and ethanol, of which propylene glycol is particularly preferred.

It is advantageous when 5 to 25% by weight of an organic solvent is incorporated into the composition. The following table shows quantitatively how the solubility of the meglumine-azosemide and of the triethanolamine-azosemide salt can be substantially increased by the addition of organic solvents e.g. of propylene glycol, to the water for injection purposes. Corresponding values for the sodium-azosemide salt are also given in the table for comparison.

TABLE 1

| Cation | pH value | organic solvent additive in % by weight | Concentration of the azosemide in mg/ml |
|---|---|---|---|
| Sodium | 8.0 | — | 1.7 |
|  | 10.0 | — | 2.01 |
|  | 8.0 | 10 | 3.5 |
|  | 10.0 | 10 | 5.5 |
| Meglumine | 9.0 | — | 5.1 |
|  | 9.0 | 10 | 11.8 |
| Triethanolamine | 9.8 | 10 | 10.0 |

When the meglumine-azosemide salt is used it is possible to reach the upper limit (20 mg/1 ml solution) of the usable concentration of active substance in the solution according to the invention at a pH value of about 10 and at a proportion of organic solvent of almost 25% by weight—as shown by extrapolation on the basis of the values listed in the table. In this case the usual safety margin to the maximum solubility is maintained. A safety margin to the saturation solubility should always be adhered to in the development of injection solutions since the pharmaceutical agent is also transported in winter, i.e. possibly at very low temperatures and precipitations of the active substance can occur under these circumstances. Since the precipitated active substance must then redissolve very rapidly when heated to room temperature, the safety margin to the maximum solubility should be at least 20 to 30%.

The injection solutions preferably have titration basicities which are lower than about 0.3 val/1 ml injection solution (corresponding to 0.3 mmol HCl/ml) i.e. it should be possible to bring the normal ampoule content of 10 ml injection solution to the pH value of blood of 7.4 by the addition of at most about 30 ml 0.1 normal hydrochloric acid. In contrast the pH values and titration basicities of the injections solutions disclosed in DE 24 23 550 and in the article mentioned above (pH: 10.6–11, titration basicity: >0.3 mmol HCl/ml and pH: 11–12, titration basicity: 0.4–0.5 mmol HCl/ml) were not high. Aqueous solutions of the sodium azosemide salt containing 10% propylene glycol were tested in animal experiments. They had a poor venous tolerance and were therefore unsuitable for administration to humans.

It is favourable when the buffer capacity in the solution is adjusted to < about 0.1 mmol/ml injection solution. It is advantageous to use a compound from the group sodium carbonate, arginine sodium phosphate, N-methyl-glucosamine and Trometamol as the buffer. However, in principle it is possible to also use other pharmacologically compatible buffers.

The solutions produced according to the invention which start with a suspension of azosemide in water, if desired, with addition of an organic solvent, have 0 to 10 particles/ml after the sterilization with a diameter of >10 μm as shown by particle measurements and 0 to 1 particle/ml with a diameter of >25 μm i.e. these ready-for-injection azosemide injection solutions have a very low particle number compared to solutions prepared from lyophilisates.

Although the result of the process in which the injection solution is produced from a lyophilisate can be substantially improved when, according to the inventions a water-organic solvent mixture is used instead of water as the solvent because then solutions can be produced which are much more highly concentrated than when only water is used. One must, however, still take into consideration the aforementioned disadvantages of the production via a lyophilisate as an intermediate product and the relatively high particle number.

Further advantageous embodiments of the solution according to the invention and of the process according to the invention are disclosed in the subclaims.

In a preferred process for the production of the injection solutions according to the invention, micronized azosemide with a particle size of preferably >=20 μm is suspended in a mixture composed of water for injection purposes and an organic solvent and dissolved by reaction with substances which are also added to the mixture such as meglumine and triethanolamine with salt formation. The required pH value is set. If necessary buffer is also added. The meglumine-azosemide salt has the best solubility and the lowest equivalent point (the equivalent point of the meglumine salt is at pH 8.6) of all the said salts. Subsequently it is sterilized by filtration, filled into ampoules and the injection solution is sterilized preferably for 20 minutes at 121° C. Propylene glycol, polyethylene glycol (preferably polyethylene glycol 400) and ethanol are added as organic solvents, of which propylene glycol is particularly suitable. Depending on the required concentration of active substance and on the set pH value, about 5 to ca. 25% by weight of solvent is added. Ca. 20 to 200 mg/10 ml ampoule of the active substance is preferably used. The solutions produced in this way are stable for at least three years without turbidity or decomposition. The injection solutions according to the invention can also be mixed with a 5% glucose infusion solution or with an isotonic saline solution and subsequently infused. The solutions according to the invention are stable, clear and have a good venous tolerance even at high concentrations of active substance. Representative particle measurements yielded the following values: particles with a diameter of $>=10$ μm: 0–10 particles/ml; particles with a diameter of $>=25$ μm: 0–1 particle/ml.

The following examples of operation, in which the process described in the previous paragraph was used, serve to elucidate the invention in more detail and disclose the properties of the solutions according to the invention.

EXAMPLE 1

Azosemide 100 Mg/10 Ml Injection Solution with N-Methylglucosamine 80 l water for injection purposes is mixed with 10 l propylene glycol in a sterile 100 l V2A double-cased tank provided with a stirrer. 650 g N-methylglucosamine is dissolved therein and heated to 40°–50° C. 1 kg azosemide is dissolved at 40°–50° C. while stirring. Afterwards it is filled up to 100 l with water for injection purposes. The solution has a pH value of 8.8– 9.0. The solution is filtered sterile via a membrane filter with a pore size of 0.2 μm. The sterile filtered solution is dispensed into ampoules in aliquots of 10.2 ml. The ampoules that have been filled and closed are sterilized for 20 minutes at 121° C. in an autoclave.

In this way a clear, well-tolerated, ready-to-inject injection solution is obtained which can be stored for at least three years without turbidity or decomposition.

The pH value of this solution is 8.95. The titration basicity corresponds to 0.006 mmol HCl/ml injection solution which is necessary to lower the pH value of the injection solution from 8.95 to 7.4 (pH value of blood).

EXAMPLE 2

Azosemide 20 Mg/2 Ml Injection Solution with Triethanolamine 15 l water for injection purposes and 2 l propylene glycol are mixed in a sterile 20 l V2A double-cased tank provided with a stirrer. 98 g triethanolamine is dissolved in this mixture and the solution is heated to 40°–50° C. 200 g azosemide is added while stirring and it is dissolved and filled up to 20 l with water for injection purposes.

The solution is sterile filtered via a membrane filter with a pore size of 0.2 μm, dispensed into ampoules in aliquots of 2.2 ml and the closed ampoules are sterilized for 20 minutes at 121° C. in an autoclave.

The pH value of the solution is 9.8. The titration basicity corresponds to 0.05 mmol HCl/ml injection solution which is necessary to lower the pH value from 9.8 to 7.4.

EXAMPLE 3

Azosemide 20 Mg/2 Ml Injection Solution with N-Methylglucosamine 80 l water for injection purposes is mixed with 10 l propylene glycol in a sterile 100 l V2A double-cased tank provided with a stirrer. 526.4 g N-methylglucosamine and 125 g sodium carbonate are dissolved therein and heated to 40° to 50° C. 1 kg azosemide is dissolved at 40° to 50° C. while stirring.

Afterwards it is made up to 100 l with water for injection purposes. The solution has a pH value of 9.2 to 9.5. The solution is filtered sterile via a membrane filter with a pore size of 0.2 μm. The sterile filtered solution is dispensed into ampoules in aliquots of 2.2 ml. The ampoules that have been filled and closed are sterilized for 20 minutes at 121° C. in an autoclave.

In this way a clear, well-tolerated, ready-to-inject injection solution is obtained which can be stored for at least three years without turbidity or decomposition.

The pH value of this solution is 9.4. The titration basicity corresponds to 0.009 mmol HCl/ml injection solution which is necessary to lower the pH value of the injection solution from 9.4 to 7.4.

A further process which can be used to produce the injection solutions according to the invention is by lyophilisation. The active substance is lyophilized in an alkaline solution and the lyophilisate is dissolved with the aid of a solvent ampoule which contains organic solvent and surfactant apart from water for injection purposes.

We claim:

1. An aqueous storage-stable injection solution in a form suitable for injection in a patient, said aqueous solution comprising a diuretic-effective amount of at least one water-soluble, physiologically acceptable azosemide salt of an organic amine and about 5 to about 25% by weight of at least one physiologically acceptable organic solvent.

2. Solution of claim 1, wherein said solution also contains a physiologically acceptable buffer.

3. Solution of claim 1, wherein the organic amine is meglumine, triethanolamine or mixtures thereof.

4. Solution of claim 3, wherein the organic solvent is propylene glycol, polyethylene glycol or ethanol.

5. Solution of claim 2, wherein the buffer is selected from the group consisting of sodium carbonate, arginine sodium phosphate, n-methylglycosamine and tris (hydroxymethyl)aminomethane (Trometamol).

6. Solution of claim 1, wherein the pH value of the solution is greater than about 7.

7. Solution of claim 1, wherein the solution has a titration basicity of at most about 0.3 mmol HCl/ml.

8. Solution of claim 6, wherein the pH value of the solution is between about 8.9 and 10.3, the solution contains a physiologically acceptable alkaline buffer, and the titration basicity of the solution is between about 0.001 and about 0.06 mmol HCl/ml injection solution.

9. An aqueous diuretic solution in a form suitable for injection into a patient said aqueous solution comprising a diuretic effective amount of an salt selected from the group consisting of the meglumine salt of azosemide, the triethanolamine salt of azosemide, and mixtures thereof, and about 5 to about 25 weight percent of an organic solvent selected from the group consisting of propylene glycol, polyethylene glycol and ethanol.

10. Solution of claim 9, said solution being in a sealed ampoule.

11. A process for producing a ready-for-injection, aqueous injection solution containing at least one water-soluble, physiologically acceptable salt of azosemide, said solution being capable of being stored at room temperature for at least three years without adverse turbidity or decomposition, said process comprising dissolving a meglumine salt, a triethanolamine salt, or mixtures thereof, of azosemide in a mixture of water and about 5 to 25 percent by weight of a physiologically acceptable organic solvent.

12. Process of claim 11, wherein the mixture contains a physiologically acceptable buffer.

13. Process of claim 11, wherein a compound with forms said salt with azosemide is dissolved in said mixture, and azosemide is suspended and dissolved with salt formation in the mixture to form said solution, and thereafter the pH value of the solution is adjusted to a value which is greater than 7.

14. Process of claim 12, wherein the buffer capacity of the solution is adjusted to a maximum of about 0.1 mmol HCl/ml injection solution.

15. Process of claim 14, wherein the buffer capacity is adjusted to a maximum of about 0.03 mmol HCl/ml injection solution.

16. Process of claim 14, wherein the injection solution is sterile filtered and filled into ampoules.

17. Process of claim 16, including the step of sterilizing the filled ampoules for about 20 minutes at about 121° C.

18. Process of claim 11, wherein the azosemide salt is lyophilized in an alkaline solution and the lyophilisate is dissolved in an injection mixture which contains an organic solvent, a surfactant, and water.

19. Solution of claim 1, wherein the azosemide salt is a salt of meglumine and the organic solvent is propylene glycol.

20. A process for increasing the concentration of azosemide in a ready-for-injection solution comprising a diuretic-effective amount of at least one water-soluble, physiologically acceptable azosemide salt of an organic amine, the process comprising adding to the water-soluble, physiologically acceptable azosemide salt of the organic amine about 5 to about 25 percent by weight of at least one physiologically acceptable organic solvent.

21. The process of claim 20, wherein the concentration of azosemide in the ready-for-injection solution is at least 2 mg/ml.

22. The process of claim 20, wherein the salt is formed in situ between the azosemide and the organic amine.

23. A process for producing a ready-for-injection, aqueous injection solution containing at least one water-soluble, physiologically acceptable salt of azosemide, comprising dissolving a physiologically acceptable organic amine in a mixture of water and about 5 to 25 percent by weight of a physiologically acceptable organic solvent, and adding azosemide to form a physiologically acceptable azosemide salt of the organic amine.

24. A process for increasing the concentration of azosemide in a ready-for-injection solution comprising forming a mixture in water of a diuretic-effective amount of azosemide, at least one water-soluble physiologically acceptable organic amine and about 5 to about 25 percent by weight of at least one physiologically acceptable organic solvent.

* * * * *